US012790574B2

(12) United States Patent
Meng et al.

(10) Patent No.: US 12,790,574 B2
(45) Date of Patent: Nov. 10, 2026

(54) IN VITRO ANALYSIS DIAGNOSTIC INSTRUMENT, AND MICROFLUIDIC CHIP AND METHOD FOR SORTING AND ENRICHING CIRCULATING TUMOR CELLS

(71) Applicant: Guangzhou Wondfo Biotech Co., Ltd, Guangzhou (CN)

(72) Inventors: Xuan Meng, Guangzhou (CN); Jiamin Yang, Guangzhou (CN)

(73) Assignee: Guangzhou Wondfo Biotech Co., Ltd, Guangzhou (CN)

( * ) Notice: Subject to any disclaimer, the term of this patent is extended or adjusted under 35 U.S.C. 154(b) by 649 days.

(21) Appl. No.: 18/263,397

(22) PCT Filed: Jan. 26, 2022

(86) PCT No.: PCT/CN2022/073892

§ 371 (c)(1),
(2) Date: Jul. 28, 2023

(87) PCT Pub. No.: WO2022/161371

PCT Pub. Date: Aug. 4, 2022

(65) Prior Publication Data

US 2024/0084233 A1 Mar. 14, 2024

(30) Foreign Application Priority Data

Jan. 29, 2021 (CN) ........................ 202110128093.6

(51) Int. Cl.
*B01L 3/00* (2006.01)
*C12M 1/00* (2006.01)
(Continued)

(52) U.S. Cl.
CPC ............ *C12M 23/16* (2013.01); *C12M 47/04* (2013.01); *C12N 5/0693* (2013.01)

(58) Field of Classification Search
None
See application file for complete search history.

(56) References Cited

U.S. PATENT DOCUMENTS

2009/0014360 A1 1/2009 Toner et al.
2012/0292233 A1 11/2012 Toner et al.
(Continued)

FOREIGN PATENT DOCUMENTS

CN 104797340 A 7/2015
CN 105854967 A 8/2016
(Continued)

OTHER PUBLICATIONS

CN105854967—English Translation (Year: 2016).*
(Continued)

*Primary Examiner* — Rebecca M Giere
(74) *Attorney, Agent, or Firm* — Maier & Maier, PLLC

(57) ABSTRACT

An in vitro analysis diagnostic instrument, and a microfluidic chip and method for sorting and enriching circulating tumor cells. The microfluidic chip includes a functional board. A first side face of the functional board is provided with a primary sorting channel in communication with a sample inlet and a fine screening channel in communication with the primary sorting channel, and a deepened channel is dug on the side of the fine screening channel away from the aggregation of circulating tumor cells. The deepened channel is arranged in an extension direction of the fine screening channel, and the deepened channel has a depth greater than that of the fine screening channel.

15 Claims, 6 Drawing Sheets

(51) Int. Cl.

| | |
|---|---|
| ***C12M 3/06*** | (2006.01) |
| ***C12N 5/09*** | (2010.01) |

(56) References Cited

U.S. PATENT DOCUMENTS

| | | | |
|---|---|---|---|
| 2017/0333902 | A1 | 11/2017 | Masaeli et al. |
| 2018/0128723 | A1 | 5/2018 | Ryu et al. |
| 2020/0171488 | A1 | 6/2020 | Han et al. |

FOREIGN PATENT DOCUMENTS

| | | | |
|---|---|---|---|
| CN | 107699478 | A | 2/2018 |
| CN | 109082368 | A | 12/2018 |
| CN | 109967150 | A | 7/2019 |
| CN | 110106069 | A | 8/2019 |
| CN | 111330656 | A | 6/2020 |
| CN | 111763606 | A | 10/2020 |
| CN | 112268934 | A | 1/2021 |
| CN | 112547145 | A | 3/2021 |

OTHER PUBLICATIONS

Extended European Search Report issued on Oct. 29, 2024, in corresponding European Application No. 22745247.1, 7 pages.
Extended European Search Report issued on Nov. 4, 2024, in corresponding European Application No. 22745245.5, 8 pages.
International Search Report issued on May 7, 2022, in corresponding International Application No. PCT /CN2022/073892, 8 pages.
Lei Wang et al. "High-Throughput Inertial Focusing of Micrometer- and Sub-Micrometer•Sized Particles Separation", Advanced Science, vol. 4, No. 10, May 30, 2017 (May 30, 2017), article No. 1700153, pp. 1-11, 11 pages.

* cited by examiner

IN VITRO ANALYSIS DIAGNOSTIC INSTRUMENT, AND MICROFLUIDIC CHIP AND METHOD FOR SORTING AND ENRICHING CIRCULATING TUMOR CELLS

FIELD

The present invention relates to the technical field of cell sorting, and in particular to an in vitro analysis diagnostic instrument, and a microfluidic chip and method for sorting and enriching circulating tumor cells.

BACKGROUND

Cancer is the second most common cause of death worldwide, accounting for 1 in 6 deaths from cancer. Tumor metastasis is responsible for 90% of cancer deaths. The tumor metastasis is a process in which tumor cells are detached from the primary focus or a metastatic focus, circulate in the lymphatic system or peripheral blood to invade distant tissues, form a new tumor focus, and eventually lead to the death of the patient. These detached tumor cells are called circulating tumor cells (CTCs). Therefore, by checking the number and types of circulating tumor cells in the blood, the dynamic changes of tumor lesions can be monitored and the therapeutic effect can be evaluated. Immunophenotyping and genome sequencing analysis of the isolated circulating tumor cells can find drug targets, so as to achieve personalized and precise treatment. Circulating tumor cells are also extremely important for early screening of tumors. When tumors are 1-2 mm in size, imaging and other means are difficult to detect them. But in the early stages of many cancers, the blood contains a certain number of circulating tumor cells. For some high-risk patients, regular detection of circulating tumor cells is helpful for early detection and treatment of cancer, and for prevention of disease progression.

Therefore, it is particularly important to sort and enrich circulating tumor cells from the blood, but the content of circulating tumor cells is extremely low. In general, there are 1-10 circulating tumor cells per milliliter of blood, and millions of white blood cells and billions of red blood cells per milliliter, so that the difficulty of sorting and enriching circulating tumor cells is like finding a needle in a haystack. The technologies for sorting and enriching circulating tumor cells are roughly divided into: immunomagnetic bead method, density gradient centrifugation method, membrane filtration method, and microfluidic chip technology. The circulating tumor cells and the white blood cells in a channel of the conventional microfluidic chip are likely to overlap, which is not conducive to the recovery of circulating tumor cells.

SUMMARY

On this basis, it is necessary to address the above problems and provide an in vitro analysis diagnostic instrument, and a microfluidic chip and method for sorting and enriching circulating tumor cells, which can effectively avoid the overlapping of circulating tumor cells and white blood cells, and facilitate the recovery of circulating tumor cells.

A microfluidic chip for sorting and enriching circulating tumor cells comprises a functional board, a first side face of the functional board being provided with:

a primary sorting channel, which is in communication with a sample inlet and is configured to preliminarily aggregate circulating tumor cells and white blood cells in a sample; and a fine screening channel, which is in communication with the primary sorting channel, wherein a deepened channel is dug on the side of the fine screening channel away from the aggregation of the circulating tumor cells, the deepened channel is arranged in an extension direction of the fine screening channel, and the deepened channel has a depth greater than that of the fine screening channel.

According to the microfluidic chip for sorting and enriching circulating tumor cells as described above, the blood sample is diluted and passed through the sample inlet into the primary sorting channel. Due to the stress influence of inertial lift force, Dean drag force, etc., red blood cells flow disorderly in the primary sorting channel due to their smaller diameters, while the white blood cells and the circulating tumor cells are preliminarily aggregated into bands due to their larger diameters under the balance of acting forces in the primary sorting channel, and then flow into the fine screening channel. The circulating tumor cells are just aggregated into a thin band and are close to the bottom of an inner wall of the fine screening channel, while the white blood cells have not yet aggregated at the bottom of the inner wall of the channel, but the white blood cells are very close to the band aggregated by the circulating tumor cells. By digging a deepened channel in the fine screening channel on the side away from the aggregation of the circulating tumor cells, the deepened channel is arranged in the extension direction of the fine screening channel and the depth of the deepened channel is greater than that of the fine screening channel, to disrupt the liquid flow state near an outer wall of the fine screening channel, so that the inertial lift force and the Dean drag force are changed, destroying the original balance, the white blood cells can produce a disordered motion state, and the white blood cells are thus more evenly distributed in the fine screening channel, preventing a band aggregated by the white blood cells from overlapping with the circulating tumor cells. Similarly, the red blood cells are also distributed more evenly, not only ensuring that the aggregation of the circulating tumor cells is not disturbed, but also preventing the white blood cells from being aggregated at the bottom of the inner wall of the fine screening channel, so that the subsequent separation of the circulating tumor cells from the white blood cells is facilitated, and the recovery of the circulating tumor cells is facilitated.

In one embodiment, the depth of the deepened channel is 50 μm-200 μm greater than the depth of the fine screening channel; or the depth of the deepened channel is 70 μm-120 μm greater than the depth of the fine screening channel.

In one embodiment, the fine screening channel is designed such that a ratio of the size of the circulating tumor cells to a hydraulic diameter is less than or equal to 0.5; or the fine screening channel is designed such that the ratio of the size of the circulating tumor cells to the hydraulic diameter is less than or equal to 0.07; or the fine screening channel is designed such that the ratio of the size of the circulating tumor cells to the hydraulic diameter is 0.045 to 0.065; or the fine screening channel is designed such that the ratio of the size of the circulating tumor cells to the hydraulic diameter is 0.05 to 0.06.

In one embodiment, the first side face of the functional board is further provided with a first turning channel having a radius of curvature greater than that of the fine screening channel, the first turning channel is in communication with the fine screening channel, and the deepened channel correspondingly extends into the first turning channel and is located on the side away from the aggregation of the circulating tumor cells.

In one embodiment, the first side face of the functional board is further provided with a removal channel, the removal channel is in communication with the end of the first turning channel away from the fine screening channel, the deepened channel correspondingly extends into the removal channel and is located on the side away from the aggregation of the circulating tumor cells, and the removal channel is provided with a shunt hole penetrating a wall face of the removal channel.

In one embodiment, the first side face of the functional board is further provided with a second turning channel having a radius of curvature greater than that of the removal channel, the second turning channel is in communication with the end of the removal channel away from the first turning channel, and the deepened channel correspondingly extends into the second turning channel and is located on the side away from the aggregation of the circulating tumor cells.

In one embodiment, the end of the second turning channel away from the removal channel is provided with a recovery channel and a waste liquid channel that are independent of each other, the recovery channel is in communication with the side of the second turning channel close to the aggregation of the circulating tumor cells, and the waste liquid channel is in communication with the side of the second turning channel close to the deepened channel.

In one embodiment, a ratio of proportions of liquid flowing out of the waste liquid channel and the recovery channel is 45%-65%:3%-20%; or the ratio of proportions of liquid flowing out of the waste liquid channel and the recovery channel is 50%-60%:5%-10%.

In one embodiment, the waste liquid channel and the recovery channel are each of a repeatedly folded structure.

In one embodiment, a second side face of the functional board is provided with a buffer channel of a repeatedly folded structure, and the buffer channel is in communication with the shunt hole.

In one embodiment, a proportion of liquid flowing out of the buffer channel is 30%-70%; or the proportion of liquid flowing out of the buffer channel is 45%-60%.

In one embodiment, a blocking member is provided in the removal channel corresponding to an inlet of the shunt hole, the blocking member is located on the side of the shunt hole away from the deepened channel, and the blocking member has a width in an extension direction of the removal channel that is greater than a diameter of the shunt hole.

In one embodiment, a plurality of shunt holes are provided in sequence in an extension direction of the removal channel, a second side face of the functional board is provided with a plurality of buffer channels of a repeatedly folded structure, and the buffer channels are in communication with the shunt holes in one-to-one correspondence; and a blocking member is provided in the removal channel corresponding to an inlet of the shunt hole, the blocking member is located on the side of the shunt hole away from the deepened channel, and the blocking member has a width in an extension direction of the removal channel that is greater than a diameter of the shunt hole.

In one embodiment, along a flow direction of the sample, the plurality of shunt holes have a gradually increasing distance from the corresponding deepened channel.

In one embodiment, along a flow direction of the sample, the buffer channel corresponding to the shunt hole close to the first turning channel has a length greater than that of other buffer channels.

In one embodiment, the primary sorting channel comprises an introduction section, a connection section and a sorting section in sequential communication with one another, the end of the introduction section away from the connection section is in communication with the sample inlet, and the introduction section is of a repeatedly folded structure.

In one embodiment, the connection section comprises a first straight pipe section, a first arc-shaped section, a second straight pipe section, a second arc-shaped section and a third straight pipe section in sequential communication with one another, the first straight pipe section is connected to the end of the introduction section away from the sample inlet, and the third straight pipe section is connected to the sorting section.

In one embodiment, an end of the introduction section is arranged in a clockwise direction and is connected to the first straight pipe section.

In one embodiment, the sorting section comprises a joining section and a main pipe section in sequential communication with each other, the joining section is connected to the third straight pipe section, the main pipe section is connected to the fine screening channel, the joining section has a width a in a direction perpendicular to its extension direction, the main pipe section has a width b in a direction perpendicular to its extension direction, where $a<b$, and the sorting section is a wave-shaped passage that is not symmetrical in a width direction thereof.

In one embodiment, the fine screening channel and the removal channel are sinusoidal arc-shaped channels.

In one embodiment, the microfluidic chip for sorting and enriching circulating tumor cells further comprises an upper cover plate and a lower cover plate, wherein the upper cover plate is provided with the sample inlet, and the upper cover plate overlaps and is connected to the first side face of the functional board; the lower cover plate is provided with a recovery hole, a waste liquid hole and a discharge hole, and the lower cover plate overlaps and is connected to the second side face of the functional board; and the recovery channel is in communication with the recovery hole, the waste liquid channel is in communication with the waste liquid hole, and the shunt hole is in communication with the discharge hole.

A method for sorting and enriching circulating tumor cells comprises the steps of:

passing a diluted blood sample into a sample inlet of a microfluidic chip, and preliminarily aggregating circulating tumor cells and white blood cells of the blood sample after the blood sample passes through a primary sorting channel of a repeatedly folded structure, wherein the circulating tumor cells are aggregated into a thin band and are close to the bottom of an inner wall of the primary sorting channel, the white blood cells have not yet aggregated at the bottom of the inner wall of the primary sorting channel, and red blood cells are dispersed in the primary sorting channel; and introducing the blood sample from the primary sorting channel into a fine screening channel, wherein a deepened channel is dug on the side of the fine screening channel away from the aggregation of the circulating tumor cells, the circulating tumor cells in the blood sample are aggregated into a thin band and are close to the bottom of an inner wall of the fine screening channel, and the white blood cells are in a disordered motion state and are far away from the bottom of the inner wall of the fine screening channel.

According to the method for sorting and enriching circulating tumor cells as described above, the blood sample is diluted and passed through the sample inlet into the primary sorting channel. Due to the stress influence of inertial lift force, Dean drag force, etc., red blood cells flow disorderly in the primary sorting channel due to their smaller diameters, while the white blood cells and the circulating tumor cells are preliminarily aggregated into bands due to their larger diameters under the balance of acting forces in the primary sorting channel, and then flow into the fine screening channel. The circulating tumor cells are just aggregated into a thin band and are close to the bottom of an inner wall of the fine screening channel, while the white blood cells have not yet aggregated at the bottom of the inner wall of the channel, but the white blood cells are very close to the band aggregated by the circulating tumor cells. By digging a deepened channel in the fine screening channel on the side away from the aggregation of the circulating tumor cells, the deepened channel is arranged in the extension direction of the fine screening channel and the depth of the deepened channel is greater than that of the fine screening channel, to disrupt the liquid flow state near an outer wall of the fine screening channel, so that the inertial lift force and the Dean drag force are changed, destroying the original balance, the white blood cells can produce a disordered motion state, and the white blood cells are thus more evenly distributed in the fine screening channel, preventing a band aggregated by the white blood cells from overlapping with the circulating tumor cells. Similarly, the red blood cells are also distributed more evenly, not only ensuring that the aggregation of the circulating tumor cells is not disturbed, but also preventing the white blood cells from being aggregated at the bottom of the inner wall of the fine screening channel, so that the subsequent separation of the circulating tumor cells from the white blood cells is facilitated, and the recovery of the circulating tumor cells is facilitated.

In one embodiment, the method for sorting and enriching circulating tumor cells further comprises the steps of:

introducing the blood sample from the fine screening channel into a first turning channel having a radius of curvature greater than that of the fine screening channel, wherein the circulating tumor cells in the blood sample are aggregated into a thin band and are further close to the bottom of an inner wall of the first turning channel; introducing the blood sample from the first turning channel into a removal channel having a shunt hole, wherein the red blood cells and the white blood cells in the blood sample flow out of the removal channel through the shunt hole, and the circulating tumor cells in the blood sample are aggregated into a thin band and are close to the bottom of an inner wall of the removal channel;

introducing the remaining blood sample after passing through the removal channel into a second turning channel having a radius of curvature greater than that of the removal channel, wherein the circulating tumor cells in the blood sample are aggregated into a thin band and are further close to the bottom of an inner wall of the second turning channel; and communicating a recovery channel with the second turning channel on the side close to the aggregation of the circulating tumor cells for recovering the blood sample on this side, and communicating a waste liquid channel with the second turning channel on the other side for collecting the blood sample on this side.

The method for sorting and enriching circulating tumor cells further comprises the step of:

passing the blood sample recovered by the recovery channel into the sample inlet of the microfluidic chip again, and repeating the above steps.

In one embodiment, in the method for sorting and enriching circulating tumor cells, a blocking member is provided in the removal channel corresponding to an inlet of the shunt hole, the blocking member is located on the side of the shunt hole away from the deepened channel, and the blocking member has a width in an extension direction of the removal channel that is greater than a diameter of the shunt hole; and a proportion of the blood sample flowing out of the shunt hole is 30%-70%, and a proportion of the blood sample flowing out of the waste liquid channel is 45%-65%.

An in vitro analysis diagnostic instrument comprises a main body and a microfluidic chip for sorting and enriching circulating tumor cells according to any one of the above embodiments, wherein the microfluidic chip for sorting and enriching circulating tumor cells are usable together with the main body.

In one embodiment, the main body is provided with a chip mounting position for mounting the microfluidic chip for sorting and enriching circulating tumor cells, a mixing chamber for mixing a sample, a diluent and a lysate, and a recovery chamber for recovering the circulating tumor cells, wherein the mixing chamber is capable of being in communication with a sample inlet of the microfluidic chip for sorting and enriching circulating tumor cells, and the recovery chamber is capable of being in communication with a recovery hole through which the circulating tumor cells flow out of the microfluidic chip for sorting and enriching circulating tumor cells.

In one embodiment, the in vitro analysis diagnostic instrument further comprises a power system and a control system, wherein the control system is configured to control the power system to inject the sample, the diluent and the lysate into the mixing chamber at a specific ratio and to pass the mixed liquid from the mixing chamber into the microfluidic chip for sorting and enriching circulating tumor cells at a flow velocity.

In one embodiment, the in vitro analysis diagnostic instrument further comprises a first control valve, wherein the main body is further provided with a cleaning solution chamber, a sample chamber, a diluent chamber and a lysate chamber; the cleaning solution chamber, the sample chamber, the diluent chamber and the lysate chamber are respectively connected to the power system; and the first control valve has one end connected to outlets of the cleaning solution chamber, the sample chamber, the diluent chamber and the lysate chamber, and the other end connected to the mixing chamber.

In one embodiment, the in vitro analysis diagnostic instrument further comprises a second control valve, wherein the second control valve has one end connected to the mixing chamber, and the other end connected to the recovery chamber, and the recovery chamber is further connected to the power system.

LIST OF REFERENCE SIGNS

01. Red blood cell; 02. White blood cell; 03. Circulating tumor cell; 1. Functional board; 10. Primary sorting channel; 11. Sample intake hole; 110. Introduction section; 112. Straight pipe section; 114. Curved pipe section, 116. Long straight pipe; 118. Short straight pipe, 120. Connection section; 121. First straight pipe section; 122. First arc-shaped section; 123. Second straight pipe section; 124. Second arc-shaped section; 125. Third straight pipe section; 130. Sorting section; 132. Joining section; 13. First curved pipe unit; 13*a*. First side wall; 13*b*. Second side wall; 14. Second curved pipe unit, 14*a*. Third side wall; 14*b*. Fourth side wall; 134. Main pipe section; 15. Third curved pipe unit; Fifth side wall 15*a* and sixth side wall 15*b*, 16. Fourth curved pipe unit, 16*a*. Seventh side wall; 16*b*. Eighth side wall; 20. Fine screening channel; 30. Deepened channel; 40. First turning channel; 50. Removal channel; 51. Shunt hole; 52. Blocking member; 60. Second turning channel; 70. Recovery channel; 71. First outflow hole; 80. Waste liquid channel; 81. Second outflow hole; 90. Buffer channel; 2. Upper cover plate; 21. Sample inlet; 3. Lower cover plate; 31. Recovery hole; 32. Waste liquid hole; 33. Discharge hole.

DETAILED DESCRIPTION OF THE PREFERRED EMBODIMENTS

In order to make the above objectives, features and advantages of the present invention more clearly understood, particular embodiments of the present invention will be described in detail below with reference to the accompanying drawings. In the following description, numerous specific details are set forth in order to fully understand the present invention. However, the present invention can be implemented in numerous other ways that are different from those described herein, a person skilled in the art can make similar improvements without departing from the connotation of the present invention, and therefore the present invention is not limited to the particular embodiments disclosed below.

Referring to FIGS. 1-4, a microfluidic chip for sorting and enriching circulating tumor cells provided in an embodiment comprises a functional board 1. Further, the microfluidic chip for sorting and enriching circulating tumor cells further comprises an upper cover plate 2 and a lower cover plate 3. The upper cover plate 2 is superimposed on and connected to a first side face of the functional board 1, the lower cover plate 3 is superimposed on and connected to a second side face of the functional board 1, and the upper cover plate 2 is provided with a sample inlet 21.

Figure 1:
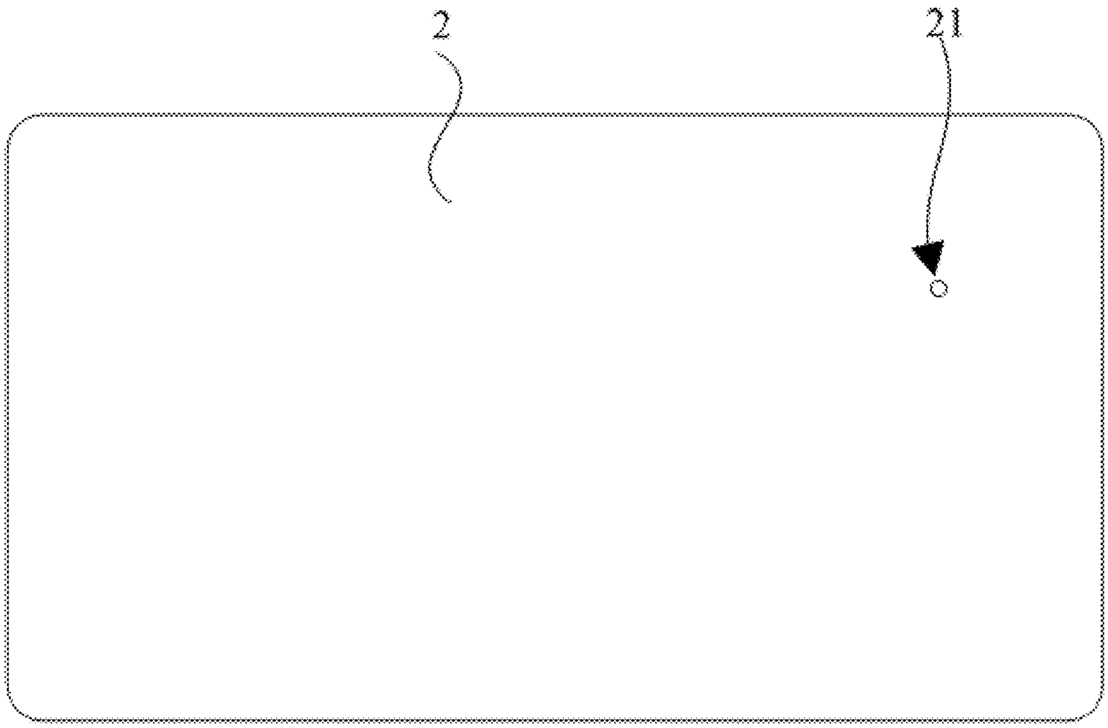
FIG. 1 is a schematic diagram of an upper cover plate of a microfluidic chip for sorting and enriching circulating tumor cells in an embodiment.
Figure 2:
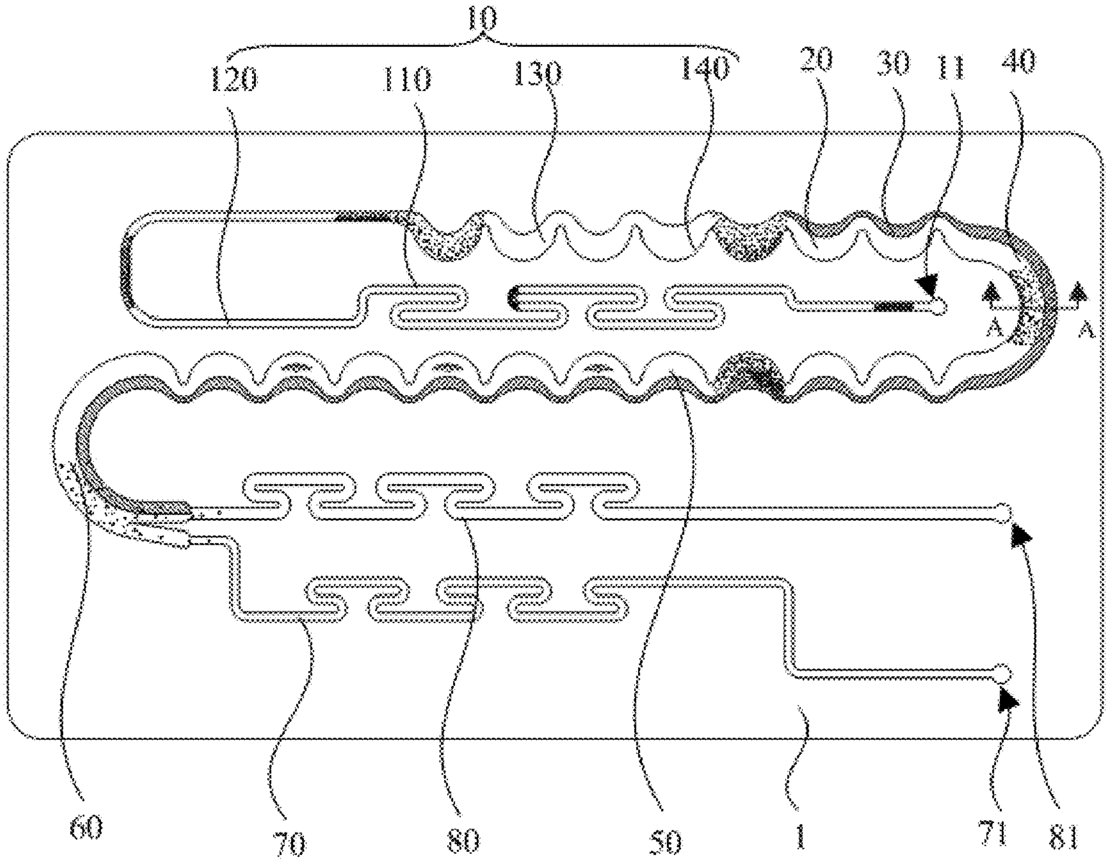
FIG. 2 is a schematic diagram of a first side face of a functional board of a microfluidic chip for sorting and enriching circulating tumor cells in an embodiment.
Figure 6:
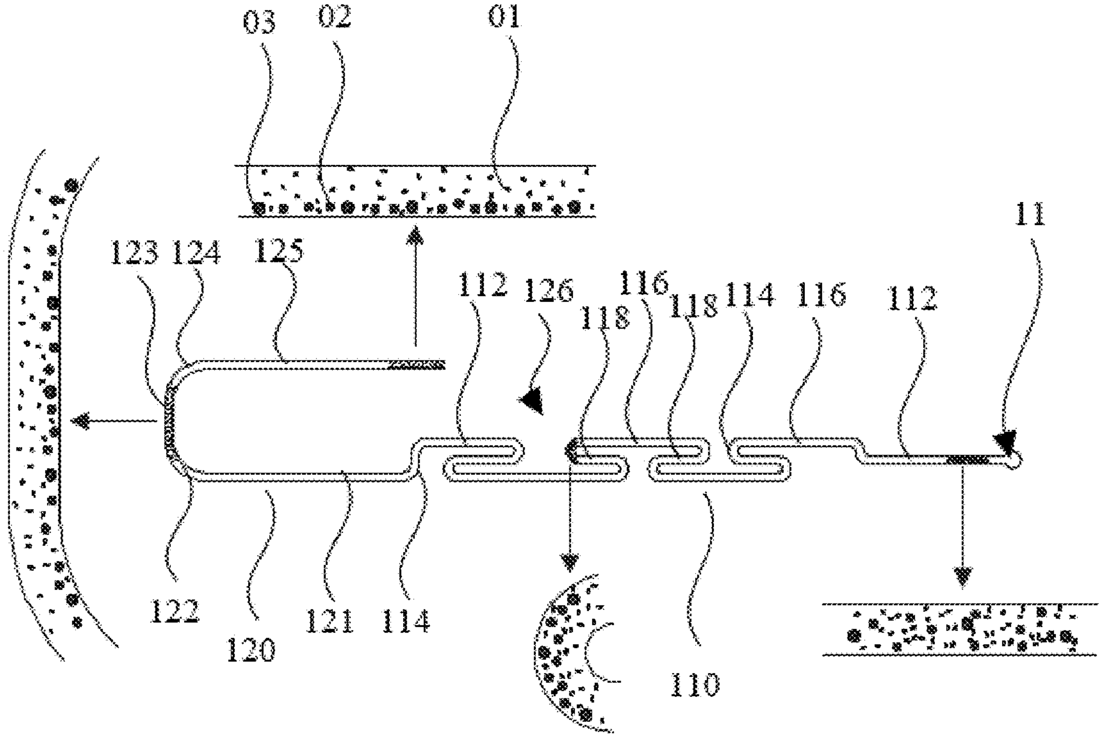
FIG. 6 is a schematic diagram of motion states of circulating tumor cells, white blood cells, and red blood cells of a blood sample in an introduction section and a connection section of a primary sorting channel.
Figure 7:
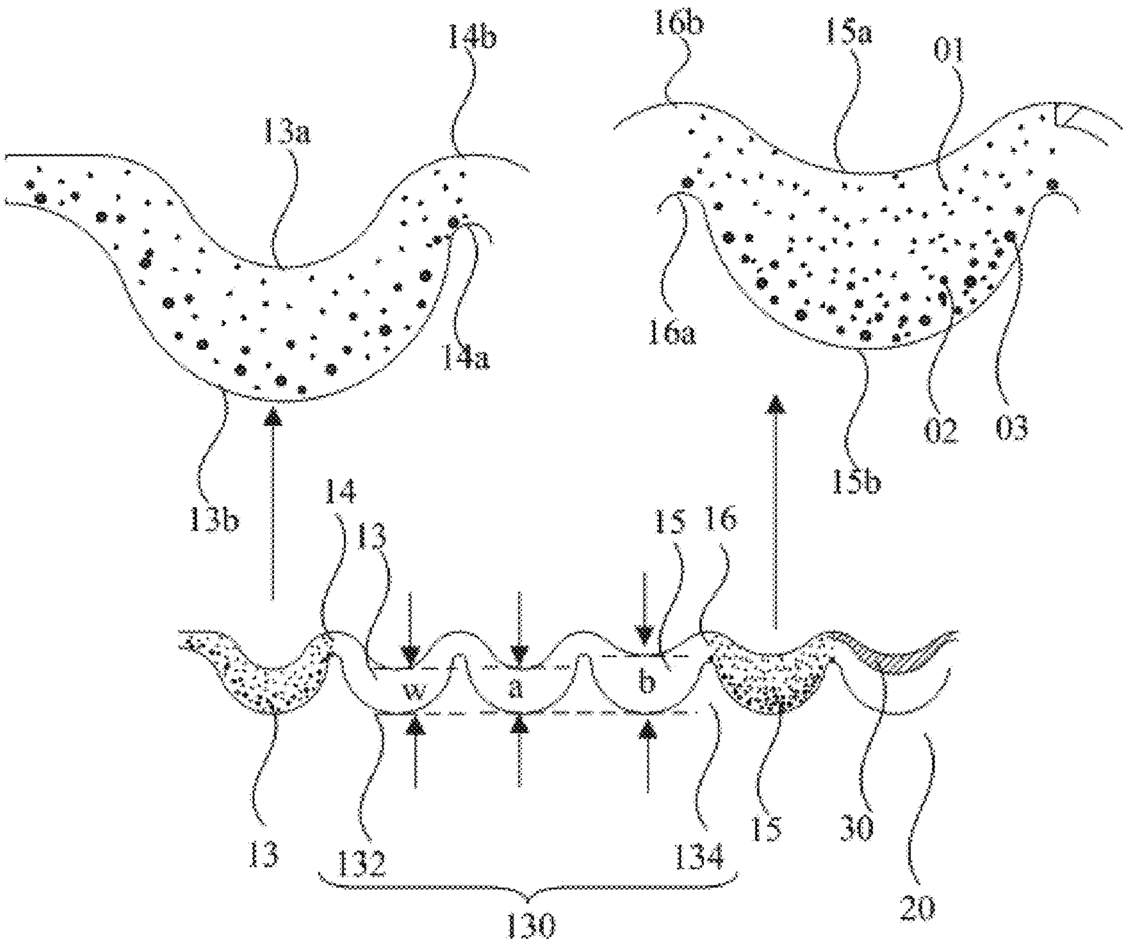
FIG. 7 is a schematic diagram of motion states of circulating tumor cells, white blood cells, and red blood cells of a blood sample in a sorting section of a primary sorting channel.

Referring to FIGS. 2, 6 and 7, the first side face of the functional board 1 is provided with a primary sorting channel 10 and a fine screening channel 20. The primary sorting channel 10 is in communication with the sample inlet 21 and is configured to preliminarily aggregate circulating tumor cells 03 and white blood cells 02 in a sample. The fine screening channel 20 is in communication with the primary sorting channel 10, and a deepened channel 30 is dug on the side of the fine screening channel 20 away from the aggregation of the circulating tumor cells 03. The deepened channel 30 is arranged in an extension direction of the fine screening channel 20, and the deepened channel 30 has a depth greater than that of the fine screening channel 20.

The diluted blood sample is passed into the microfluidic chip through the sample inlet 21 of the upper cover plate 2, and flows into the primary sorting channel 10 through a sample intake hole 11 in the functional board 1. The sample intake hole 11 penetrates the first side face and the second side face of the functional board 1, and is arranged corresponding to the sample inlet 21. Due to the stress influence of inertial lift force, Dean drag force, etc., referring to FIG. 6, red blood cells 01 of the sample flow disorderly in the primary sorting channel 10 due to their smaller diameters, while the white blood cells 02 and the circulating tumor cells 03 are preliminarily aggregated into bands due to their larger diameters under the balance of acting forces in the primary sorting channel 10, and then flow into the fine screening channel 20. Referring to FIG. 7, at this time, the circulating tumor cells 03 are just aggregated into a thin band and are close to the bottom of an inner wall of the fine screening channel 20, while the white blood cells 02 have not yet aggregated at the bottom of the inner wall of the channel, but the white blood cells 02 are very close to the band aggregated by the circulating tumor cells 03. By digging a deepened channel 30 in the fine screening channel 20 on the side away from the aggregation of the circulating tumor cells 03, the deepened channel 30 is arranged in the extension direction of the fine screening channel 20 and the depth of the deepened channel 30 is greater than that of the fine screening channel 20, to disrupt the liquid flow state near an outer wall of the fine screening channel 20, so that the inertial lift force and the Dean drag force are changed, destroying the original balance, the white blood cells 02 can produce a disordered motion state, and the white blood cells 02 are thus more evenly distributed in the fine screening channel 20, preventing a band aggregated by the white blood cells 02 from overlapping with the circulating tumor cells 03. Similarly, the red blood cells 01 are also distributed more evenly, not only ensuring that the aggregation of the circulating tumor cells 03 is not disturbed, but also preventing the white blood cells 02 from being aggregated at the bottom of the inner wall of the fine screening channel 20, so that the subsequent separation of the circulating tumor cells 03 from the white blood cells 02 is facilitated, and the recovery of the circulating tumor cells 03 is facilitated.

Referring to FIGS. 2 and 7, in one embodiment, the fine screening channel is an asymmetric wave-shaped passage with alternately arranged large turns and small turns. In other embodiments, the fine screening channel may also be configured as a straight passage.

Specifically, in one embodiment, the fine screening channel is an asymmetric wave-shaped passage having a rectangular cross-section whose aspect ratio varies over the length of the passage resulting in the formation of a single stream of aggregated particles.

Optionally, the aspect ratio of the rectangular cross-section varies between 8 and 30. In another embodiment, the aspect ratio of the rectangular cross-section varies between 11 and 23.

Optionally, in one embodiment, the fine screening channel is designed such that a ratio of the size of the circulating tumor cells to a hydraulic diameter is less than or equal to 0.5. Alternatively, the fine screening channel is designed such that the ratio of the size of the circulating tumor cells to the hydraulic diameter is less than or equal to 0.07. Alternatively, the fine screening channel is designed such that the ratio of the size of the circulating tumor cells to the hydraulic diameter is 0.045 to 0.065. Alternatively, the fine screening channel is designed such that the ratio of the size of the circulating tumor cells to the hydraulic diameter is 0.05 to 0.06. The hydraulic diameter Dh is defined as 2wh/(w+h), referring to FIGS. 5 and 7, where w and h are the width and height of the channel.

Figure 5:
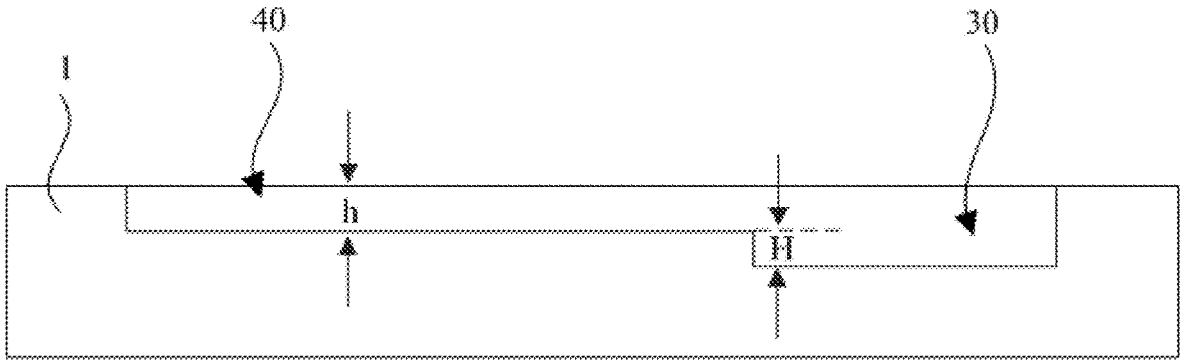
FIG. 5 is a schematic cross-sectional view along section line A-A in FIG. 2.
Figure 8:
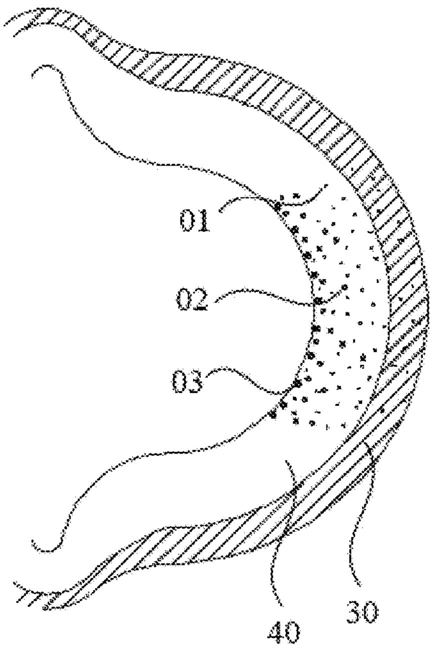
FIG. 8 is a schematic diagram of motion states of circulating tumor cells, white blood cells, and red blood cells of a blood sample in a first turning channel.

Further, referring to FIGS. 2 and 8, in one embodiment, the first side face of the functional board 1 is further provided with a first turning channel 40. The first turning channel 40 has a radius of curvature greater than that of the fine screening channel 20, and the first turning channel 40 is in communication with the fine screening channel 20. Referring to FIG. 5, the deepened channel 30 correspondingly extends into the first turning channel 40 and is located on the side away from the aggregation of the circulating tumor cells 03. Under the action of the deepened channel 30, the white blood cells 02 are distributed more evenly in the first turning channel 40 to avoid overlapping with the circulating tumor cells 03. Since a first turning channel 40 is connected to the fine screening channel 20 and the radius of the first turning channel 40 is large, the relative advantage of the inertial lift force is even greater. When passing through the first turning channel 40, the fluid in the middle of the channel is subject to the largest centrifugal force, and thus flows to an outside edge of the passage. The fluid near the wall of the passage has the smallest flow velocity and is thus subjected to the smallest centrifugal force, so it is squeezed by the fluid in the middle. Therefore, under the action of the first turning channel 40, the circulating tumor cells 03 can be as close as possible to the bottom of the inner wall of the channel, preparing for the subsequent sorting of the circulating tumor cells 03 and the discharge of the white blood cells 02.

Referring to FIGS. 2 and 5, optionally, the depth of the deepened channel 30 is 50 μm-200 μm greater than the depth of the fine screening channel 20. Optionally, the fine screening channel has a depth of 100 μm-200 μm. Preferably, the depth of the deepened channel 30 is 70 μm-120 μm greater than the depth of the fine screening channel 20. Preferably, the fine screening channel has a depth of 110 μm-150 μm. FIG. 5 is a schematic cross-sectional view of the deepened channel 30 in the first turning channel 40. The fine screening channel 20 extends to and is connected to the first turning channel 40, and the first turning channel 40 is also correspondingly provided with a deepened channel 30. The depth difference H between the deepened channel 30 and the first turning channel 40 is 50 μm-200 μm, and preferably 70 μm-120 μm. It can not only ensure that the circulating tumor cells 03 can flow in the fine screening channel 20 or the first turning channel 40 as close as possible to the bottom of the inner wall of the channel, but also disturb the flow state of the liquid on one side of the deepened channel 30 to prevent a band aggregated by the white blood cells 02 from overlapping with the circulating tumor cells 03, affecting the subsequent recovery rate and purity of the circulating tumor cells 03.

Referring to FIGS. 2 and 6, in one embodiment, the primary sorting channel 10 comprises an introduction section 110, a connection section 120 and a sorting section 130 in sequential communication with one another, the end of the introduction section 110 away from the connection section 120 is in communication with the sample inlet 21, and the introduction section 110 is of a repeatedly folded structure. Referring to FIG. 6, when the sample enters an inlet end of the introduction section 110, the red blood cells 01, the white blood cells 02 and the circulating tumor cells 03 are evenly distributed in the channel. The diameter of the red blood cells 01 is about 6-8 μm, the diameter of the white blood cells 02 is about 8-12 μm, and the diameter of the circulating tumor cells 03 is about 20-30 μm. When the liquid flows through several bends of the introduction section 110, the white blood cells 02 and the circulating tumor cells 03 are slowly aggregated, while the red blood cells 01 are still evenly distributed. As the liquid flows through the longer connection section 120, the bands aggregated by the white blood cells 02 and the circulating tumor cells 03 become thinner. When the liquid is about to enter the sorting section 130, the bands aggregated by the white blood cells 02 and the circulating tumor cells 03 become thinner and are close to the inner wall of the primary sorting channel 10. The configuration of the introduction section 110 as a repeatedly folded structure can not only buffer the inflow of the blood sample, but also make the flow state of the liquid more stable, and the flow of the blood sample through the introduction section 110 and the connection section 120 facilitates the aggregation of the circulating tumor cells 03 and the white blood cells 02 into bands in this channel.

Compared with the sorting section 130, the introduction section 110 and the connection section 120 are elongated channels. Optionally, the widths of the introduction section 110 and the connection section 120 are 0.3 mm-1.2 mm. Preferably, the widths of the introduction section 110 and the connection section 120 are 0.5 mm-0.9 mm. Optionally, the depths of the introduction section 110 and the connection section 120 are 0.06 mm-0.3 mm. Preferably, the depths of the introduction section 110 and the connection section 120 are 0.1 mm-0.2 mm. With such a setting, the flow velocity of the blood sample entering the primary sorting channel 10 tends to be stable, and at the same time, the circulating tumor cells 03 and the white blood cells 02 can be preliminarily aggregated into bands, facilitating the subsequent sorting of the circulating tumor cells 03.

Specifically, referring to FIG. 6, in an embodiment, the introduction section 110 comprises a plurality of straight pipe sections 112 and a plurality of curved pipe sections 114, two adjacent straight pipe sections 112 are connected to each other via one curved pipe section 114, and the first one of the straight pipe sections 112 is in communication with the sample inlet 21 through the sample intake hole 11, and the last one of the curved pipe sections 114 is arranged in a clockwise direction and is connected to the connection section 120. Such an arrangement makes the introduction section 110 form multiple bends, so that the speed of the blood sample gradually stabilizes, providing a buffering effect and facilitating the preliminary aggregation of the white blood cells 02 and the circulating tumor cells 03. The manufacturing difficulty is also easier than that of a spiral channel, and the overall size of the chip can be designed to be smaller. In other embodiments, in order to achieve the buffering purpose, the introduction section 110 may also be configured in an "S" shape, a spiral shape or other shapes that are repeatedly folded. With the last one of the curved pipe sections 114 of the introduction section 110 being arranged in a clockwise direction and being connected to the connection section 120, the main purpose is to enable the circulating tumor cells 03 to be always aggregated on the side where the inner wall of the channel is located during the subsequent sorting process.

In an embodiment, the straight pipe section 112 between the first one of the straight pipe sections 112 and the last one of the curved pipe sections 114 comprises alternately arranged long straight pipes 116 and short straight pipes 118. Two ends of one long straight pipe 116 (such as a lower long straight pipe 116) are connected to two short straight pipes 118 via the curved pipe sections 114 arranged in the clockwise direction. Alternatively, two ends of one long straight pipe 116 (such as an upper long straight pipe 116) are connected to two short straight pipes 118 via the curved pipe sections 114 arranged in the counterclockwise direction. Clockwise and counterclockwise are determined along the flow direction of the sample. By alternately arranging the long straight pipes 116 and the short straight pipes 118, the straight pipe sections 112 are arranged in multiple rows in a direction perpendicular to the flow direction of the sample, and the position of the channel is arranged reasonably, facilitating the reduction of the length and width of the chip.

Further, the long straight pipes 116 and the short straight pipes 118 are arranged in parallel to each other, in the flow direction of the sample, the adjacent two long straight pipes 116 and the short straight pipes 118 between the two long straight pipes 116 are arranged at intervals in the width direction of the straight pipe section 112. The long straight pipe 116 and the short straight pipe 118 are connected to each other via a 180° curved pipe section 114, the long straight pipe 116 and the short straight pipe 118 are arranged in parallel to each other, and the straight pipe sections 112 are arranged in three rows in the width direction of the straight pipe section 112.

Specifically, referring to FIG. 6, the first one (at the inlet end of the introduction section 110) of the straight pipe sections 112 is connected to one long straight pipe 116 in sequence via a curved pipe section 114 arranged in the clockwise direction and a curved pipe section 114 arranged in the counterclockwise direction. The last one of the straight pipe sections 112 is connected to the connection section 120 in sequence via a curved pipe section 114 arranged in the counterclockwise direction and a curved pipe section 114 arranged in the clockwise direction. When flowing into the connection section 120, the sample flows in the clockwise direction, facilitating the preliminary aggregation of the circulating tumor cells 03 into a band on one side of the inner wall of the channel.

Referring to FIGS. 2 and 6, in one embodiment, the connection section 120 comprises a first straight pipe section 121, a first arc-shaped section 122, a second straight pipe section 123, a second arc-shaped section 124 and a third straight pipe section 125 in sequential communication with one another, the first straight pipe section 121 is connected to the end of the introduction section 110 away from the sample inlet 21, and the third straight pipe section 125 is connected to the sorting section 130. Specifically, an end of the introduction section 110 is arranged in the clockwise direction and is connected to the first straight pipe section 121 so that circulating tumor cells 03 are always aggregated at the inner wall of the channel. The connection section 120 functions to connect the introduction section 110 and the sorting section 130. The blood sample flows in the clockwise direction from the end of the introduction section 110 through the first straight pipe section 121, the first arc-shaped section 122, the second straight pipe section 123, the second arc-shaped section 124 and the third straight pipe section 125, and the bands aggregated by the white blood cells 02 and the circulating tumor cells 03 gradually become thinner. When the liquid is in the third straight pipe section 125 and is about to enter the sorting section 130, the bands aggregated by the white blood cells 02 and the circulating tumor cells 03 become thinner and are close to the inner wall of the channel. In one embodiment, the first arc-shaped section 122 is a 90° arc-shaped section arranged in the clockwise direction, and the second arc-shaped section 124 is a 90° arc-shaped section arranged in the clockwise direction. The first straight pipe section 121 and the third straight pipe section 125 are arranged vertically spaced apart from each other, and the third straight pipe section 125 is located above the first straight pipe section 121.

Further, a first area 126 is enclosed between an extension line of the first straight pipe section 121 and an extension line of the third straight pipe section 125, and the introduction section 110 is repeatedly folded within the range of the first area. By rationally arranging the position of each section of the channel and making full use of the volume of the chip, it is convenient to miniaturize the overall size of the chip, and it is also convenient for the preliminary aggregation of the white blood cells 02 and the circulating tumor cells 03 into bands.

Referring to FIGS. 2 and 7, in one embodiment, the sorting section 130 comprises a joining section 132 and a main pipe section 134 in sequential communication with each other, the joining section 132 is connected to the third straight pipe section 125, the main pipe section 134 is connected to the fine screening channel 20, the joining section 132 has a width a in a direction perpendicular to its extension direction, the main pipe section 134 has a width b in a direction perpendicular to its extension direction, where a<b, and the sorting section 130 is a wave-shaped passage that is not symmetrical in a width direction thereof. In order to avoid that when the blood sample enters the wave-shaped sorting section 130 from the elongated connection section 120, the width of the channel suddenly becomes larger, disrupting the original motion trajectory of the circulating tumor cells 03, and avoiding destroying the original trajectory of the circulating tumor cells 03 moving near the inner wall. By configuring a joining section 132 having a width smaller than that of the main pipe section 134 to be transitioned to the main pipe section 134 so as to provide a buffering function, it is avoided that it is necessary for the circulating tumor cells 03 to flow through more wave-shaped main pipe sections 134 for aggregation into a thin band close to the inner wall of the channel, and it is also possible to shorten the length of main pipe section 134.

Referring to FIG. 7, specifically, the joining section 132 comprises first curved pipe units 13 and second curved pipe units 14 arranged alternately. The first curved pipe units 13 have a radius of curvature greater than that of the second curved pipe units 14. The main pipe section 134 comprises third curved pipe units 15 and fourth curved pipe units 16 arranged alternately. The third curved pipe units 15 have a radius of curvature greater than that of the fourth curved pipe units 16, and the last one of the second curved pipe units 14 is connected to the first one of the third curved pipe units 15. a is the width of the first curved pipe unit 13 in a direction perpendicular to its extension direction, and b is the width of the third curved pipe unit 15 in a direction perpendicular to its extension direction. The joining section 132 is formed by alternately connecting the first curved pipe units 13 with a large radius of curvature and the second curved pipe units 14 with a small radius of curvature, and the main pipe section 134 is formed by alternately connecting the third curved pipe units 15 with a large radius of curvature and the fourth curved pipe units 16 with a small radius of curvature. The width of the joining section 132 in a direction perpendicular to its extension direction mainly refers to the width of the first curved pipe unit 13 in a direction perpendicular to its extension direction, and the width of the main pipe section 134 in a direction perpendicular to its extension direction mainly refers to the width of the third curved pipe unit 15 in a direction perpendicular to its extension direction. According to the factors such as the cell diameter, the height and width of the channel and the flow velocity of the liquid, and comprehensive stress analysis of the inertial lift force and the Dean drag force, the circulating tumor cells 03 are close to the bottom of the inner wall of the main pipe section 134, and the white blood cells 02 are also gradually approaching the bottom of the inner wall of the main pipe section 134. Optionally, b is 0.4 mm-1.2 mm greater than a. Preferably, b is 0.7 mm-0.9 mm greater than a.

Referring to FIG. 7, further, the first curved pipe unit 13 comprises a first side wall 13*a* and a second side wall 13*b* arranged opposite each other, and the first side wall 13*a* and the second side wall 13*b* are asymmetric curved surfaces. The second curved pipe unit 14 comprises a third side wall 14*a* and a fourth side wall 14*b* arranged opposite each other, and the third side wall 14*a* and the fourth side wall 14*b* are asymmetric curved surfaces. The third side wall 14*a* is connected to the second side wall 13*b*, and the fourth side wall 14*b* is connected to the first side wall 13*a*. The third curved pipe unit 15 comprises a fifth side wall 15*a* and a sixth side wall 15*b* arranged opposite each other, and the fifth side wall 15*a* and the sixth side wall 15*b* are asymmetric curved surfaces. The fourth curved pipe unit 16 comprises a seventh side wall 16*a* and an eighth side wall 16*b* arranged opposite each other, and the seventh side wall 16*a* and the eighth side wall 16*b* are asymmetric curved surfaces. The fifth side wall 15*a* is connected to the eighth side wall 16*b*, and the sixth side wall 15*b* is connected to the seventh side wall 16*a*. The first curved pipe unit 13 and the second curved pipe unit 14 are configured to protrude in different directions, the third curved pipe unit 15 and the fourth curved pipe unit 16 are configured to protrude in different directions, and the first curved pipe unit 13 and the third curved pipe unit 15 are configured to protrude in the same direction. Such a configuration of asymmetric curved surfaces forms an asymmetric inertial aggregation, so that the circulating tumor cells are focused at a stable position in the cross-section of the channel (the bottom of the inner wall of the channel) to form a band, forming a focused flow, which flows downstream.

Further, the radius of curvature of the first side wall 13*a* is smaller than that of the second side wall 13*b*, and the radius of curvature of the fifth side wall 15*a* is greater than that of the sixth side wall 15*b*. Therefore, the distance between the first side wall 13*a* and the second side wall 13*b* is smaller than the distance between the fifth side wall 15*a* and the sixth side wall 15*b*, so as to achieve buffering of the fluid from the joining section 132 to the main pipe section 134. Further, the radius of curvature of the third side wall 14*a* is smaller than that of the fourth side wall 14*b*. The radius of curvature of the seventh side wall 16*a* is smaller than that of the eighth side wall 16*b*.

Figure 9:
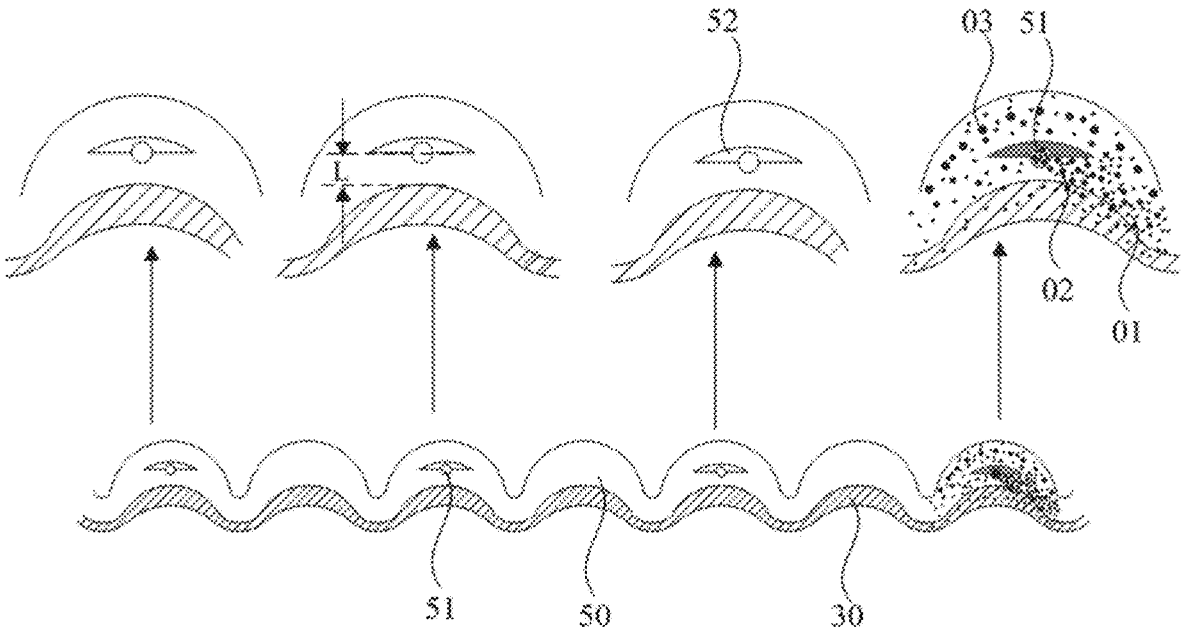
FIG. 9 is a schematic diagram of motion states of circulating tumor cells, white blood cells, and red blood cells of a blood sample in a removal channel.

Further, referring to FIGS. 2 and 9, in one embodiment, the first side face of the functional board 1 is further provided with a removal channel 50. The removal channel 50 is in communication with the end of the first turning channel 40 away from the fine screening channel 20, the deepened channel 30 correspondingly extends into the removal channel 50 and is located on the side away from the aggregation of the circulating tumor cells 03, and the removal channel 50 is provided with a shunt hole 51 penetrating a wall face of the removal channel 50. The blood continues to flow in the removal channel 50 and flows through the shunt hole 51. The circulating tumor cells 03 continue to move against the bottom of the inner wall of the removal channel 50. Since the white blood cells 02 and the red blood cells 01 are evenly distributed in the channel, some of the white blood cells 02 and the red blood cells 01 then flow out from the shunt hole 51 to facilitate subsequent recovery of the circulating tumor cells 03.

Referring to FIGS. 2, 8 and 9, as the liquid flows out from the shunt hole 51, the flow velocity of the liquid in the channel will relatively decrease, and the motion trajectory of the circulating tumor cells 03 will change slightly, and they will easily move away from the inner wall of the channel. The circulating tumor cells 03 are easy to approach the shunt hole 51, and by joining a first turning channel 40 with a large radius of curvature before the removal channel 50, the circulating tumor cells 03 flow through the largely-bent first turning channel 40 and then flow against the bottom of the inner wall of the channel to prevent the circulating tumor cells 03 from flowing into the shunt hole 51 and increase the recovery rate of the circulating tumor cells 03.

Figure 3:
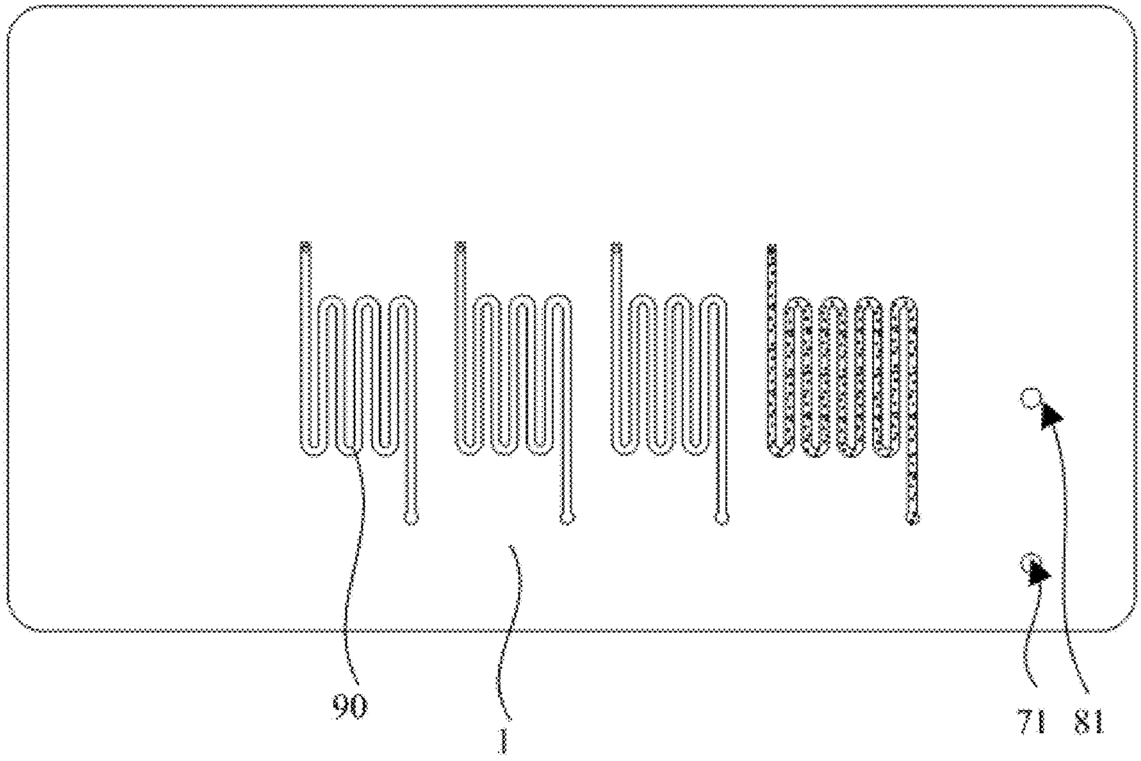
FIG. 3 is a schematic diagram of a second side face of a functional board of a microfluidic chip for sorting and enriching circulating tumor cells in an embodiment.
Figure 4:
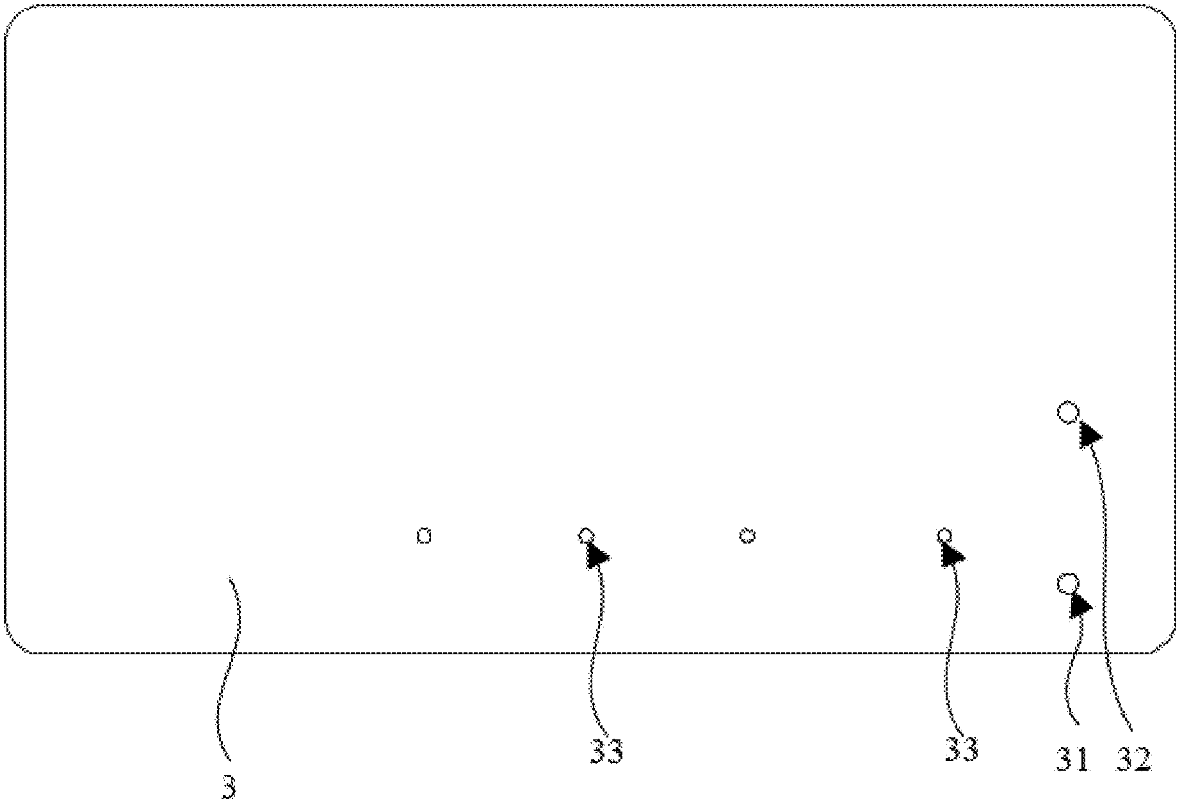
FIG. 4 is a schematic diagram of a lower cover plate of a microfluidic chip for sorting and enriching circulating tumor cells in an embodiment.

Referring to FIGS. 2 and 3, further, in one embodiment, a second side face of the functional board 1 is provided with a buffer channel 90 of a repeatedly folded structure, and the buffer channel 90 is in communication with the shunt hole 51. The buffer channel 90 is designed as a repeatedly folded structure, so that the state of the liquid flowing out of the removal channel 50 is stable, and the flow of the remaining liquid in the removal channel 50 is prevented from being disturbed by shaking, which affects the subsequent recovery of the circulating tumor cells 03.

The length of the buffer channel 90 can control the amount of discharged liquid. The length of the buffer channel 90 and the position of the shunt hole 51 are used to adjust the amount of the white blood cells 02 and the red blood cells 01 discharged and control the motion trajectory of the circulating tumor cells 03. In an embodiment, the proportion of the white blood cells 02 and the red blood cells 01 removed through the shunt hole 51 is 30%-70%, and preferably 45%-60%. Similarly, the proportion of the liquid flowing out of the shunt hole 51 is 30%-70%, and the optimal range is 45%-60%. With such a setting, the liquid outflow is less than 70%, and the final flow velocity is relatively reduced by no more than 70%, so as to avoid affecting the original motion trajectory of the circulating tumor cells 03, making it difficult for some circulating tumor cells 03 to be recovered, resulting in a decrease in the final recovery rate.

Referring to FIGS. 2 and 9, in one embodiment, a blocking member 52 is provided in the removal channel 50 corresponding to an inlet of the shunt hole 51, the blocking member 52 is located on the side of the shunt hole 51 away from the deepened channel 30, and the blocking member 52 has a width in an extension direction of the removal channel

50 that is greater than a diameter of the shunt hole 51. The blocking member 52 protects the circulating tumor cells 03 from flowing into the shunt hole 51. Since the white blood cells 02 and the red blood cells 01 are evenly distributed in the channel, the white blood cells 02 and the red blood cells 01 flow out from the shunt hole 51, flow perpendicularly into the second side face of the functional board 1, and flow into the buffer channel 90.

Further, the blocking member 52 is arranged to protrude from the wall face of the removal channel 50, that is, the height of the position where the blocking member 52 is located is higher than other positions of the removal channel 50, providing a blocking between the circulating tumor cells 03 and the shunt hole 51, and preventing the circulating tumor cells 03 from flowing out from the shunt hole 51. The side of the blocking member 52 close to the aggregation of the circulating tumor cells 03 is an arc-shaped wall, and a bending direction of the arc-shaped wall is consistent with a bending direction of a side wall of the removal channel 50 on the side close to the aggregation of the circulating tumor cells 03. The side of the blocking member 52 close to the aggregation of the circulating tumor cells 03 is an arc-shaped wall, which matches the band aggregated by the circulating tumor cells 03, so that the influence of the blocking member 52 on the aggregation of the circulating tumor cells 03 is consistent, avoiding disturbing the aggregation of the circulating tumor cells 03.

Optionally, the blocking member 52 and the functional board 1 are of an integrally formed structure, and the blocking member 52 is formed by a protruding portion reserved during the formation of the removal channel 50. The middle part of the side of the blocking member 52 away from the arc-shaped wall is arranged around the outer periphery of the corresponding side of the shunt hole 51. The white blood cells 02 and the red blood cells 01 flowing toward the shunt hole 51 are blocked by the side wall of the blocking member 52 away from the arc-shaped wall, and finally flow into the shunt hole 51.

Referring to FIGS. 2, 3, and 9, in one embodiment, a plurality of shunt holes 51 are provided in sequence in the extension direction of the removal channel 50, the second side face of the functional board 1 is provided with a plurality of buffer channels 90 of a repeatedly folded structure, and the buffer channels 90 are in communication with the shunt holes 51 in one-to-one correspondence. The plurality of shunt holes 51 provided in the flow direction of the liquid remove the white blood cells 02 and the red blood cells 01 multiple times, facilitating the subsequent recovery of the circulating tumor cells 03. Since there is no need to aggregate the white blood cells 02 and the red blood cells 01, the width and the height of the channel may also be designed wider, facilitating the increment of the flow velocity of the liquid and the improvement of the sorting efficiency. Moreover, a blocking member 52 is provided in the removal channel 50 at an inlet of each corresponding shunt hole 51, the blocking member 52 is located on the side of the shunt hole 51 away from the deepened channel 30, and the blocking member 52 has a width in an extension direction of the removal channel 50 that is greater than a diameter of the shunt hole 51. The blocking member 52 protects the circulating tumor cells 03 from flowing into the shunt hole 51, and the white blood cells 02 and the red blood cells 01 flow out from the shunt hole 51, flow perpendicularly into the second side face of the functional board 1, and flow into the buffer channel 90.

Referring to FIG. 9, in one embodiment, along the flow direction of the sample, the plurality of shunt holes 51 have a gradually increasing distance L from the corresponding deepened channel 30. With the discharge of the liquid, the white blood cells 02 and the red blood cells 01 will gradually flow to the side away from the deepened channel 30, corresponding to the flow direction of the sample, the shunt hole 51 is gradually arranged in a direction away from the deepened channel 30, facilitating the outflow of the white blood cells 02 and the red blood cells 01 from the subsequent shunt holes 51.

In one embodiment, along the flow direction of the sample, the buffer channel 90 corresponding to the shunt hole 51 close to the first turning channel 40 has a length greater than that of other buffer channels 90. Referring to FIG. 3, it can be seen that the length of the buffer channel 90 corresponding to the first shunt hole 51 is designed longer than the others. Since the amount of liquid flowing into the first shunt hole 51 will be more than other shunt holes 51, the buffer channel 90 is designed to be longer, so that more liquid can flow out of the buffer channel 90, and the outflow liquid tends to be stable, avoiding affecting the flow velocity of subsequent liquid and disturbing the flow of the circulating tumor cells 03.

In one embodiment, the fine screening channel 20 and the removal channel 50 are sinusoidal arc-shaped channels. When the fluid flows in an arc-shaped passage, the fluid flowing in a parabola has the highest velocity in the middle of the passage. When passing through the turning point of the passage, the fluid in the middle of the micro passage is subjected to the largest centrifugal force because of its maximum flow velocity, and thus flows to the outer side wall of the arc-shaped passage. The fluid near the wall of the passage has the smallest flow velocity and is thus subjected to the smallest centrifugal force, so it is squeezed by the fluid having the high flow velocity in the middle. In order to maintain mass conservation everywhere in the fluid, in the direction perpendicular to the fluid flow, a pair of counter-rotating and symmetrical vortices are formed, which are respectively located at the upper and lower portions of the cross-section of the passage, thereby generating the secondary flow of Dean vortices. The Dean vortices will have a drag effect on the particles in the fluid, which is called Dean drag force. In the arc-shaped passage, the flowing particles will be affected by both the inertial lift force and the Dean drag force, and the relative magnitude of these two forces determines the focused flow of the particles flowing in the arc-shaped passage. In this embodiment, due to the inertial lift force and the Dean drag force in the fine screening channel 20 and the removal channel 50, the circulating tumor cells 03 are focused into a band at the inner wall of the channel.

Figure 10:
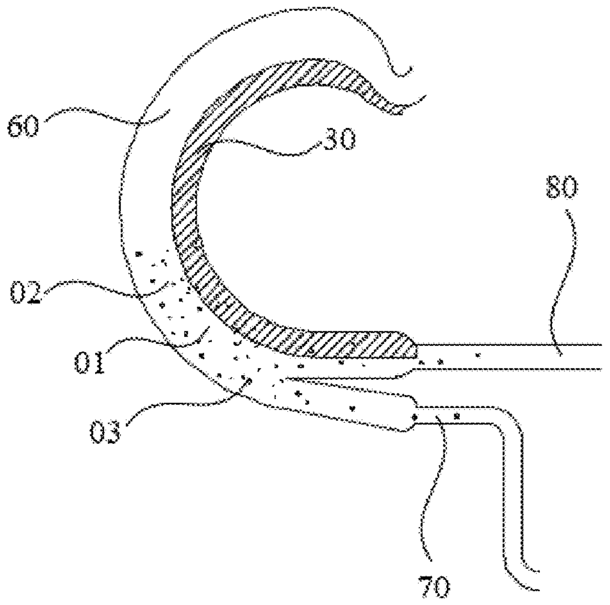
FIG. 10 is a schematic diagram of motion states of circulating tumor cells, white blood cells, and red blood cells of a blood sample in a second turning channel.

Further, referring to FIGS. 2 and 10, in one embodiment, the first side face of the functional board 1 is further provided with a second turning channel 60. The second turning channel 60 has a radius of curvature greater than that of the removal channel 50, the second turning channel 60 is in communication with the end of the removal channel 50 away from the first turning channel 40, and the deepened channel 30 correspondingly extends into the second turning channel 60 and is located on the side away from the aggregation of the circulating tumor cells 03. After the blood flows through the shunt hole 51, the contents of the white blood cells 02 and the red blood cells 01 gradually decrease, and at the same time, the flow velocities thereof also gradually decrease. The joining of the second turning channel 60 having a radius of curvature greater than that of the removal channel 50 can stabilize the motion trajectory of the circulating tumor cells 03 and facilitate the subsequent recovery of the circulating tumor cells 03.

Referring to FIG. 10, in one embodiment, the end of the second turning channel 60 away from the removal channel 50 is provided with a recovery channel 70 and a waste liquid channel 80 that are independent of each other, the recovery channel 70 is in communication with the side of the second turning channel 60 close to the aggregation of the circulating tumor cells 03, and the waste liquid channel is in communication with the side of the second turning channel 60 close to the deepened channel 30. The circulating tumor cells 03 flow against the inner wall of the second turning channel 60 into the recovery channel 70, while the white blood cells 02 and the red blood cells 01 flow into the waste liquid channel 80. In one embodiment, the waste liquid channel and the recovery channel 70 are of a repeatedly folded structure to stabilize the flow state of the liquid and prevent the subsequent falling of the liquid from the waste liquid hole 32 and the recovery hole 31, effecting the motion trajectory of the circulating tumor cells 03 at the end of the second turning channel 60.

By adjusting the lengths and the depths of the waste liquid channel and the recovery channel 70, the volume proportions of the two can be adjusted, thereby adjusting the proportions of the white blood cells 02 and the red blood cells 01 removed. In one embodiment, the proportion of liquid flowing out of the waste liquid channel is 45%-65%, and preferably 50%-60%. The proportion of liquid flowing out of the recovery channel 70 is 3%-20%, and preferably 5%-10%. In the liquid collected from the recovery hole 31, the recovery rate of the circulating tumor cells 03 may reach 90% or more, and the removal rate of the white blood cells 02 and the red blood cells 01 is 90% or more. Returning the recovered liquid to the chip for circulation and filtration for multiple times can further increase the removal rate of the white blood cells 02 and the red blood cells 01, and improve the recovery purity of the circulating tumor cells 03.

Referring to FIGS. 1-4, in one embodiment, the upper cover plate 2 is bonded to the first side face of the functional board 1, and the lower cover plate 3 is bonded to the second side face of the functional board 1, so that the channels on the first side face and the second side face of the functional board 1 form a sealed passage. The upper cover plate 2 is provided with the sample inlet 21 that is in communication with the primary sorting channel 10 on the first side face of the functional board 1, so as to facilitate the introduction of the blood sample into the microfluidic chip from the sample inlet 21. The lower cover plate 3 is provided with a recovery hole 31, a waste liquid hole 32 and a discharge hole 33. The shunt hole 51 is in communication with the discharge hole 33, and some of the white blood cells 02 and the red blood cells 01 in the removal channel 50 flow from the shunt hole 51 to the second side face of the functional board 1, and flow out of the microfluidic chip from the discharge hole 33 of the lower cover plate 3. The recovery channel 70 is in communication with the recovery hole 31 through a first outflow hole 71 penetrating the first side face and the second side face of the functional board, and the sorted circulating tumor cells 03 flow out of the microfluidic chip through the recovery hole 31 of the lower cover plate 3. The waste liquid channel is in communication with the waste liquid hole 32 through a second outflow hole 81 penetrating the first side face and the second side face of the functional board, and the other remaining liquid flows out of the microfluidic chip through the waste liquid hole 32 of the lower cover plate 3.

The conventional microfluidic chips for sorting and enriching circulating tumor cells 03 are basically made of PDMS. Such a chip is expensive and cannot be reused, resulting in that each test costs thousands of yuan. However, most cancer deaths worldwide occur in low- and middle-income countries, so developing an inexpensive detection product is necessary. In the processing technology of PDMS chips, channels can only designed on one side, thereby limiting the development of the functions of the chips. Moreover, the PDMS chip is not conducive to making larger and deeper channels, and the multi-level flow state of the liquid in this chip cannot be studied, and the smaller and thinner channels of PDMS also limit the flow velocity of the liquid in the chip.

The material of the microfluidic chip in the above embodiments is not limited, and materials such as PMMA, PC, ABS and glass may be used. This chip can be used repeatedly, does not need antigen/antibody, and does not need magnetic beads, thereby greatly reducing the cost. Since this chip only aggregates the circulating tumor cells 03, and does not aggregate the white blood cells 02 and the red blood cells 01, the height and the width of the channel in the chip can be larger, and the blood sample can be diluted by a large multiple, so that the flow velocity of the liquid can be increased and the detection time can be reduced.

The design strategy of this chip is that the circulating tumor cells 03 are aggregated into a thin band in the channel of the chip, and by designing a deepened channel 30, the white blood cells 02 and the red blood cells 01 are evenly distributed in the chip as much as possible, facilitating the recovery of the circulating tumor cells 03. The chip design combines fundamental principles such as asymmetric inertial focusing and Dean vortices. Moreover, a multi-level design is adopted, which is conducive to the discharge of the white blood cells 02. The chip also adopts a multi-dimensional channel design, facilitating the reduction in the squeezing of the white blood cells 02 to the motion trajectory of the circulating tumor cells 03 in the chip.

In addition, the volume of the recovery channel 70 for recovering the circulating tumor cells 03 is very small, and the volume of the waste liquid channel is very large. Therefore, when recovering the tumor cells, the white blood cells 02 and the red blood cells 01 can be indirectly removed. Due to the high recovery rate of the circulating tumor cell 03 of this chip, multiple times of filtration can be performed. As a result, less circulating tumor cells 03 are reduced on the whole, and the white blood cells 02 are almost completely removed after repeated filtration.

An embodiment of the present application also provides a method for sorting and enriching circulating tumor cells, which can be implemented by using a microfluidic chip for sorting and enriching circulating tumor cells according to any one of the above embodiments. The method for sorting and enriching circulating tumor cells in this embodiment comprises the following steps.

Referring to FIGS. 1-4, in S100, a diluted blood sample is passed into a sample inlet 21 of a microfluidic chip, and circulating tumor cells 03 and white blood cells 02 of the blood sample are preliminarily aggregated after the blood sample passes through a primary sorting channel 10 of a repeatedly folded structure. The circulating tumor cells 03 are aggregated into a thin band and are close to the bottom of an inner wall of the primary sorting channel 10, the white blood cells 02 have not yet aggregated at the bottom of the inner wall of the primary sorting channel 10, and red blood cells 01 are dispersed in the primary sorting channel 10.

In S200, the blood sample is introduced from the primary sorting channel 10 into a fine screening channel 20. A deepened channel 30 is dug on the side of the fine screening channel 20 away from the aggregation of the circulating tumor cells 03, the circulating tumor cells 03 in the blood sample are aggregated into a thin band and are close to the bottom of an inner wall of the fine screening channel 20, and the white blood cells 02 are in a disordered motion state and are far away from the bottom of the inner wall of the fine screening channel 20.

The blood sample is diluted and passed through the sample inlet 21 into the primary sorting channel 10. Due to the stress influence of inertial lift force, Dean drag force, etc., the red blood cells 01 flow disorderly in the primary sorting channel 10 due to their smaller diameters, while the white blood cells 02 and the circulating tumor cells 03 are preliminarily aggregated into bands due to their larger diameters under the balance of acting forces in the primary sorting channel 10, and then flow into the fine screening channel 20. The circulating tumor cells 03 are just aggregated into a thin band and are close to the bottom of an inner wall of the fine screening channel 20, while the white blood cells 02 have not yet aggregated at the bottom of the inner wall of the channel, but the white blood cells 02 are very close to the band aggregated by the circulating tumor cells 03. By digging a deepened channel 30 in the fine screening channel 20 on the side away from the aggregation of the circulating tumor cells 03, the deepened channel 30 is arranged in the extension direction of the fine screening channel 20 and the depth of the deepened channel 30 is greater than that of the fine screening channel 20, to disrupt the liquid flow state near an outer wall of the fine screening channel 20, so that the inertial lift force and the Dean drag force are changed, destroying the original balance, the white blood cells 02 can produce a disordered motion state, and the white blood cells 02 are thus more evenly distributed in the fine screening channel 20, preventing a band aggregated by the white blood cells 02 from overlapping with the circulating tumor cells 03. Similarly, the red blood cells 01 are also distributed more evenly, not only ensuring that the aggregation of the circulating tumor cells 03 is not disturbed, but also preventing the white blood cells 02 from being aggregated at the bottom of the inner wall of the fine screening channel 20, so that the subsequent separation of the circulating tumor cells 03 from the white blood cells 02 is facilitated, and the recovery of the circulating tumor cells 03 is facilitated.

In one embodiment, the method for sorting and enriching circulating tumor cells further comprises the following steps.

In S300, the blood sample is introduced from the fine screening channel 20 into a first turning channel 40 having a radius of curvature greater than that of the fine screening channel 20. The circulating tumor cells 03 in the blood sample are aggregated into a thin band and are further close to the bottom of an inner wall of the first turning channel 40. Referring to FIGS. 2, 8 and 9, as the liquid will flow out from the shunt hole 51 in the subsequent step S400, the flow velocity of the liquid in the channel will relatively decrease, and the motion trajectory of the circulating tumor cells 03 will change slightly, and they will easily move away from the inner wall of the channel. The circulating tumor cells 03 are easy to approach the shunt hole 51, and by joining a first turning channel 40 with a large radius of curvature before the removal channel 50, the circulating tumor cells 03 flow through the largely-bent first turning channel 40 and then flow against the bottom of the inner wall of the channel to prevent the circulating tumor cells 03 from flowing into the shunt hole 51 and increase the recovery rate of the circulating tumor cells 03.

In S400, the blood sample is introduced from the first turning channel 40 into a removal channel 50 having a shunt hole 51. The red blood cells 01 and the white blood cells 02 in the blood sample flow out of the removal channel 50 through the shunt hole 51, and the circulating tumor cells 03 in the blood sample are aggregated into a thin band and are close to the bottom of an inner wall of the removal channel 50. The blood continues to flow in the removal channel 50 and flows through the shunt hole 51. The circulating tumor cells 03 continue to move against the bottom of the inner wall of the removal channel 50. Since the white blood cells 02 and the red blood cells 01 are evenly distributed in the channel, some of the white blood cells 02 and the red blood cells 01 then flow out from the shunt hole 51 to facilitate subsequent recovery of the circulating tumor cells 03.

In S500, the remaining blood sample after passing through the removal channel 50 is introduced into a second turning channel 60 having a radius of curvature greater than that of the removal channel 50. The circulating tumor cells 03 in the blood sample are aggregated into a thin band and are further close to the bottom of an inner wall of the second turning channel 60. The joining of the second turning channel 60 having a radius of curvature greater than that of the removal channel 50 can stabilize the motion trajectory of the circulating tumor cells 03 and facilitate the subsequent recovery of the circulating tumor cells 03.

In S600, a recovery channel 70 is communication with the second turning channel 60 on the side close to the aggregation of the circulating tumor cells 03 for recovering the blood sample on this side, and a waste liquid channel is communication with the second turning channel on the other side for collecting the blood sample on this side. The circulating tumor cells 03 flow against the inner wall of the second turning channel 60 into the recovery channel 70, while the white blood cells 02 and the red blood cells 01 flow into the waste liquid channel 80.

In one embodiment, the method for sorting and enriching circulating tumor cells further comprises the following step.

In S700, the blood sample recovered by the recovery channel 70 is passed into the sample inlet 21 of the microfluidic chip again, and the above steps S100-S600 are repeated. Repeating the circulation and filtration of the recovered liquid through the above steps S100-S600 can further increase the removal rate of the white blood cells 02 and the red blood cells 01, and improve the recovery purity of the circulating tumor cells 03.

In one embodiment, a blocking member 52 is provided in the removal channel 50 corresponding to an inlet of the shunt hole 51, the blocking member 52 is located on the side of the shunt hole 51 away from the deepened channel 30, and the blocking member 52 has a width in an extension direction of the removal channel 50 that is greater than a diameter of the shunt hole 51. The blocking member 52 is blocked between the circulating tumor cells 03 and the shunt hole 51, preventing the circulating tumor cells 03 from flowing out from the shunt hole 51.

Further, a proportion of the blood sample flowing out of the shunt hole 51 is 30%-70%. By controlling the outflow of the liquid, the liquid outflow is less than 70%, and the final flow velocity is relatively reduced by no more than 70%, so as to avoid affecting the original motion trajectory of the circulating tumor cells 03, making it difficult for some circulating tumor cells 03 to be recovered, resulting in a decrease in the final recovery rate.

Further, a proportion of the blood sample flowing out of the waste liquid channel is 45%-65%. By adjusting the lengths and the depths of the waste liquid channel and the recovery channel 70, the volume proportions of the two can be adjusted, thereby adjusting the proportions of the white blood cells 02 and the red blood cells 01 removed. The volume of the recovery channel 70 for recovering the circulating tumor cells 03 is very small, and the volume of the waste liquid channel is very large. Therefore, when recovering the tumor cells, the white blood cells 02 and the red blood cells 01 can be indirectly removed.

Figure 11:
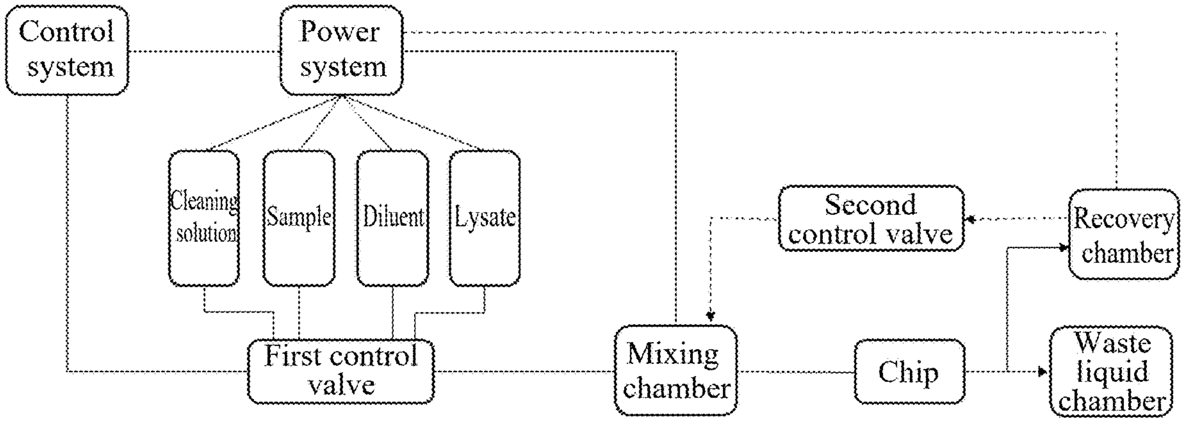
FIG. 11 is a schematic diagram of an in vitro analysis diagnostic instrument in an embodiment.

Referring to FIG. 11, an embodiment of the present application also provides an in vitro analysis diagnostic instrument, comprising a main body and a microfluidic chip for sorting and enriching circulating tumor cells according to any one of the above embodiments. The microfluidic chip for sorting and enriching circulating tumor cells can be used together with the main body. The microfluidic chip for sorting and enriching circulating tumor cells is a consumable, and is used for sorting and enriching circulating tumor cells 03 in the blood. For the same blood sample, the recovered circulating tumor cells 03 can be subjected to circulation and filtration for multiple times to improve the purity of the finally recovered circulating tumor cells 03.

In one embodiment, the main body is provided with a chip mounting position for mounting the microfluidic chip for sorting and enriching circulating tumor cells, a mixing chamber for mixing a sample, a diluent and a lysate, and a recovery chamber for recovering the circulating tumor cells, wherein the mixing chamber is capable of being in communication with a sample inlet of the microfluidic chip for sorting and enriching circulating tumor cells, and the recovery chamber is capable of being in communication with a recovery hole through which the circulating tumor cells flow out of the microfluidic chip for sorting and enriching circulating tumor cells.

In one embodiment, the in vitro analysis diagnostic instrument further comprises a power system and a control system, wherein the control system is configured to control the power system to inject the sample, the diluent and the lysate into the mixing chamber at a specific ratio and to pass the mixed liquid from the mixing chamber into the microfluidic chip for sorting and enriching circulating tumor cells at a flow velocity. The power system may be a pneumatic pump, an injection pump, etc. The mixing chamber has the function of magnetic stirring or ventilation mixing. Further, the control system is also configured to control the power system to pass a cleaning solution into the mixing chamber and the microfluidic chip for sorting and enriching circulating tumor cells in advance, to clean and remove bubbles from a connection pipeline, the mixing chamber and the chip. The control system then issues an order to control the power system to inject the sample, the diluent and the lysate into the mixing chamber at a ratio, and the liquid in the mixing chamber is passed into the microfluidic chip for sorting and enriching circulating tumor cells at a flow velocity by the power system. After the mixed liquid of the sample passes through the microfluidic chip for sorting and enriching circulating tumor cells, the circulating tumor cells are separated and enter the recovery chamber, and the rest of the liquid enters the waste liquid chamber.

In one embodiment, the in vitro analysis diagnostic instrument further comprises a first control valve, wherein the main body is further provided with a cleaning solution chamber, a sample chamber, a diluent chamber and a lysate chamber; the cleaning solution chamber, the sample chamber, the diluent chamber and the lysate chamber are respectively connected to the power system; and the first control valve has one end connected to outlets of the cleaning solution chamber, the sample chamber, the diluent chamber and the lysate chamber, and the other end connected to the mixing chamber. The power system drives the sample in the sample chamber, the diluent in the diluent chamber, and the lysate in the lysate chamber to flow toward the mixing chamber at a ratio. The first control valve controls the connection and disconnection between the cleaning solution chamber, the sample chamber, the diluent chamber and the lysate chamber and the mixing chamber.

In one embodiment, the in vitro analysis diagnostic instrument further comprises a second control valve, wherein the second control valve has one end connected to the mixing chamber, and the other end connected to the recovery chamber, and the recovery chamber is further connected to the power system. For a complex sample or a sample that requires a higher purity, the liquid in the recovery chamber may be delivered into the mixing chamber again by means of the power system and the second control valve, mixed with the diluent again, and re-introduced into the chip for a second filtration. Similarly, third and fourth filtrations may be performed. Circulating tumors with a high purity can be obtained.

In the description of the present invention, it should be understood that orientation or position relationships indicated by terms such as “center”, “longitudinal”, “transverse”, “length”, “width”, “thickness”, “up”, “down”, “front”, “rear”, “left”, “right”, “vertical”, “horizontal”, “top”, “bottom”, “inside”, “outside”, “clockwise”, “counterclockwise”, “axial”, “radial”, and “circumferential” are based on orientation or position relationships shown in the accompanying drawings and are merely for ease of description of the present invention and simplification of the description, rather than indicating or implying that the apparatuses or elements referred to must have a specific orientation or be constructed and operated in a specific orientation, and therefore cannot be construed as limiting the present invention.

In addition, the terms “first” and “second” are used for descriptive purposes only, and cannot be construed as indicating or implying relative importance or implicitly indicating the number of technical features indicated. Therefore, the features defined with “first” and “second” may explicitly or implicitly include at least one of the features. In the description of the present invention, the meaning of “a plurality of” is at least two, such as two, three and so on, unless otherwise specifically defined.

In the present invention, unless expressly stated or limited otherwise, the terms such as “mounting”, “connection”, “connected” and “fixing” should be interpreted broadly, for example, either fixed or detachable connection, or integration; may be a mechanical connection or an electrical connection; and may be a direct connection or an indirect connection by means of an intermediate medium, and may be communication between the interiors of two elements or the interaction relationship of the two elements, unless otherwise expressly defined. For those of ordinary skill in the art, the specific meaning of the terms mentioned above in the present invention should be construed according to specific circumstances.

In the present invention, unless otherwise explicitly specified and defined, the expression a first feature being “on” or “under” a second feature may be the case that the first feature is in direct contact with the second feature, or the first feature is in indirect contact with the second feature via an intermediate medium. Furthermore, the expression the first feature being “over”, “above” and “on top of” the second feature may be the case that the first feature is directly above or obliquely above the second feature, or only means that the level of the first feature is higher than the second feature. The expression the first feature being “underneath”, “below” and “beneath” the second feature may be the case that the first feature is directly below or obliquely below the second feature, or only means that the level of the first feature is less than the second feature.

It should be noted that when an element is referred to as being “fixed to” or “arranged on” another element, it may be directly on the other element or an intervening element may be present. When one element is considered to be “connected” to another element, the element may be directly connected to the another element or an intermediate element may exist simultaneously. The terms “vertical”, “horizontal”, “upper”, “lower”, “left”, “right” and similar expressions used herein are for the purpose of illustration only and do not represent any unique embodiment.

The technical features of the above embodiments may be combined arbitrarily. For the purpose of simplicity in description, all the possible combinations of the technical features in the above embodiments are not described. However, as long as there is no contradiction among the combinations of these technical features, they shall all fall within the scope of the specification.

The above embodiments merely represent several implementations of the present invention, giving specifics and details thereof, but should not be understood as limiting the scope of the present patent of invention thereby. It should be noted that a person of ordinary skill in the art could also make several alterations and improvements without departing from the spirit of the present invention and these would all fall within the scope of protection of the present invention. Therefore, the scope of protection of the present patent of invention shall be in accordance with the appended claims.

What is claimed is:

1. A microfluidic chip for sorting and enriching circulating tumor cells, comprising a functional board, a first side face of the functional board being provided with:

a primary sorting channel, which is in communication with a sample inlet and is configured to preliminarily aggregate circulating tumor cells and white blood cells in a sample; and a fine screening channel, which is in communication with the primary sorting channel, wherein a deepened channel is dug on the side of the fine screening channel away from the aggregation of the circulating tumor cells, the deepened channel is arranged in an extension direction of the fine screening channel, and the deepened channel has a depth greater than that of the fine screening channel, a first turning channel, the first turning channel having a radius of curvature greater than that of the fine screening channel, the first turning channel is in communication with the fine screening channel, and the deepened channel correspondingly extends into the first turning channel and is located on the side away from the aggregation of the circulating tumor cells, a removal channel, the removal channel is in communication with the end of the first turning channel away from the fine screening channel, the deepened channel correspondingly extends into the removal channel and is located on the side away from the aggregation of the circulating tumor cells, and the removal channel is provided with a shunt hole penetrating a wall face of the removal channel, a second turning channel, the second turning channel having a radius of curvature greater than that of the removal channel, the second turning channel is in communication with the end of the removal channel away from the first turning channel, and the deepened channel correspondingly extends into the second turning channel and is located on the side away from the aggregation of the circulating tumor cells, wherein the end of the second turning channel away from the removal channel is provided with a recovery channel and a waste liquid channel that are independent of each other, the recovery channel is in communication with the side of the second turning channel close to the aggregation of the circulating tumor cells, and the waste liquid channel is in communication with the side of the second turning channel close to the deepened channel.

2. The microfluidic chip for sorting and enriching circulating tumor cells according to claim 1, wherein the depth of the deepened channel is 50 μm-200 μm greater than the depth of the fine screening channel; or the depth of the deepened channel is 70 μm-120 μm greater than the depth of the fine screening channel.

3. The microfluidic chip for sorting and enriching circulating tumor cells according to claim 1, wherein the fine screening channel is designed such that a ratio of the size of the circulating tumor cells to a hydraulic diameter is less than or equal to 0.5; or the fine screening channel is designed such that the ratio of the size of the circulating tumor cells to the hydraulic diameter is less than or equal to 0.07; or the fine screening channel is designed such that the ratio of the size of the circulating tumor cells to the hydraulic diameter is 0.045 to 0.065; or the fine screening channel is designed such that the ratio of the size of the circulating tumor cells to the hydraulic diameter is 0.05 to 0.06.

4. The microfluidic chip for sorting and enriching circulating tumor cells according to claim 1, wherein a ratio of proportions of liquid flowing out of the waste liquid channel and the recovery channel is 45%-65%: 3%-20%; or the ratio of proportions of liquid flowing out of the waste liquid channel and the recovery channel is 50%-60%: 5%-10%.

5. The microfluidic chip for sorting and enriching circulating tumor cells according to claim 1, wherein the waste liquid channel and the recovery channel are each of a repeatedly folded structure.

6. The microfluidic chip for sorting and enriching circulating tumor cells according to claim 1, wherein a blocking member is provided in the removal channel corresponding to an inlet of the shunt hole, the blocking member is located on the side of the shunt hole away from the deepened channel, and the blocking member has a width in an extension direction of the removal channel that is greater than a diameter of the shunt hole.

7. The microfluidic chip for sorting and enriching circulating tumor cells according to claim 1, wherein a plurality of shunt holes are provided in sequence in an extension direction of the removal channel, a second side face of the functional board is provided with a plurality of buffer channels of a repeatedly folded structure, and the buffer channels are in communication with the shunt holes in one-to-one correspondence; and a blocking member is provided in the removal channel corresponding to an inlet of the shunt hole, the blocking member is located on the side of the shunt hole away from the deepened channel, and the blocking member has a width in an extension direction of the removal channel that is greater than a diameter of the shunt hole.

8. The microfluidic chip for sorting and enriching circulating tumor cells according to claim 1, wherein along a flow direction of the sample, the plurality of shunt holes have a gradually increasing distance from the corresponding deepened channel.

9. The microfluidic chip for sorting and enriching circulating tumor cells according to claim 1, wherein the fine screening channel and the removal channel are sinusoidal arc-shaped channels.

10. The microfluidic chip for sorting and enriching circulating tumor cells according to claim 1, further comprising an upper cover plate and a lower cover plate, wherein the upper cover plate is provided with the sample inlet, and the upper cover plate overlaps and is connected to the first side face of the functional board; the lower cover plate is provided with a recovery hole, a waste liquid hole and a discharge hole, and the lower cover plate overlaps and is connected to the second side face of the functional board; and the recovery channel is in communication with the recovery hole, the waste liquid channel is in communication with the waste liquid hole, and the shunt hole is in communication with the discharge hole.

11. A method for sorting and enriching circulating tumor cells, comprising the steps of:

passing a diluted blood sample into a sample inlet of a microfluidic chip to aggregate circulating tumor cells and white blood cells of the blood sample after the blood sample passes through a primary sorting channel of a repeatedly folded structure, wherein the circulating tumor cells are aggregated into a thin band and are close to the bottom of an inner wall of the primary sorting channel, the white blood cells are not aggregated at the bottom of the inner wall of the primary sorting channel, and red blood cells are dispersed in the primary sorting channel;

introducing the blood sample from the primary sorting channel into a fine screening channel, wherein a deepened channel is dug on the side of the fine screening channel away from the aggregation of the circulating tumor cells, and wherein the circulating tumor cells in the blood sample are aggregated into a thin band and are close to the bottom of an inner wall of the fine screening channel, and the white blood cells are aggregated in a disordered motion state and are far away from the bottom of the inner wall of the fine screening channel;

introducing the blood sample from the fine screening channel into a first turning channel having a radius of curvature greater than that of the fine screening channel, wherein the circulating tumor cells in the blood sample are aggregated into a thin band and are further close to the bottom of an inner wall of the first turning channel;

introducing the blood sample from the first turning channel into a removal channel having a shunt hole, wherein the red blood cells and the white blood cells in the blood sample flow out of the removal channel through the shunt hole, and the circulating tumor cells in the blood sample are aggregated into a thin band and are close to the bottom of an inner wall of the removal channel;

introducing the remaining blood sample after passing through the removal channel into a second turning channel having a radius of curvature greater than that of the removal channel, wherein the circulating tumor cells in the blood sample are aggregated into a thin band and are further close to the bottom of an inner wall of the second turning channel; and communicating a recovery channel with the second turning channel on the side close to the aggregation of the circulating tumor cells for recovering the blood sample on this side, and communicating a waste liquid channel with the second turning channel on the other side for collecting the blood sample on this side.

12. The method for sorting and enriching circulating tumor cells according to claim 11, wherein a blocking member is provided in the removal channel corresponding to an inlet of the shunt hole, the blocking member is located on the side of the shunt hole away from the deepened channel, and the blocking member has a width in an extension direction of the removal channel that is greater than a diameter of the shunt hole; and a proportion of the blood sample flowing out of the shunt hole is 30%-70%, and a proportion of the blood sample flowing out of the waste liquid channel is 45%-65%.

13. An in vitro analysis diagnostic instrument, comprising a main body and the microfluidic chip for sorting and enriching circulating tumor cells of claim 1, wherein the microfluidic chip for sorting and enriching circulating tumor cells is usable together with the main body.

14. The in vitro analysis diagnostic instrument according to claim 13, wherein the main body is provided with a chip mounting position for mounting the microfluidic chip for sorting and enriching circulating tumor cells, a mixing chamber for mixing a sample, a diluent and a lysate, and a recovery chamber for recovering the circulating tumor cells, wherein the mixing chamber is capable of being in communication with a sample inlet of the microfluidic chip for sorting and enriching circulating tumor cells, and the recovery chamber is capable of being in communication with a recovery hole through which the circulating tumor cells flow out of the microfluidic chip for sorting and enriching circulating tumor cells.

15. The in vitro analysis diagnostic instrument according to claim 14, further comprising a power system and a control system, wherein the control system is configured to control the power system to inject the sample, the diluent and the lysate into the mixing chamber at a specific ratio and to pass the mixed liquid from the mixing chamber into the microfluidic chip for sorting and enriching circulating tumor cells at a flow velocity.

* * * * *